(12) United States Patent
Simsek-Ege et al.

(10) Patent No.: US 12,725,689 B2
(45) **Date of Patent: *Sep. 1, 2026**

(54) TREATMENT PLAN IDENTIFICATION

(71) Applicant: Micron Technology, Inc., Boise, ID (US)

(72) Inventors: Fatma Arzum Simsek-Ege, Boise, ID (US); Deepti Verma, Boise, ID (US); Shruthi Kumara Vadivel, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/077,372

(22) Filed: Mar. 12, 2025

(65) Prior Publication Data

US 2025/0210169 A1 Jun. 26, 2025

Related U.S. Application Data

(63) Continuation of application No. 17/411,801, filed on Aug. 25, 2021, now Pat. No. 12,254,967.

(51) Int. Cl.

| | |
|---|---|
| ***G16H 20/00*** | (2018.01) |
| ***G16H 10/60*** | (2018.01) |
| ***G16H 50/20*** | (2018.01) |

(52) U.S. Cl.

CPC ............. *G16H 20/00* (2018.01); *G16H 10/60* (2018.01); *G16H 50/20* (2018.01)

(58) Field of Classification Search

CPC ......... G16H 20/00; G16H 10/60; G16H 50/20
See application file for complete search history.

(56) References Cited

U.S. PATENT DOCUMENTS

| | | | |
|---|---|---|---|
| 10,977,612 | B2 | 4/2021 | Yang |
| 11,055,575 | B2 | 7/2021 | Anushiravani |
| 2016/0210711 | A1 | 7/2016 | Krupa et al. |
| 2017/0148343 | A1 | 5/2017 | Merzenich et al. |
| 2017/0300662 | A1 | 10/2017 | Kumar et al. |

(Continued)

OTHER PUBLICATIONS

Carli et al., "A protocol for a multicentre, parallel-group, pragmatic randomised controlled trial to evaluate the Nevermind system in preventing and treating depression in patients with severe somatic conditions," BMC Psychiatry, Mar. 2, 2020, vol. 20, 10 pages.

*Primary Examiner* — Evangeline Barr
(74) *Attorney, Agent, or Firm* — Brooks, Cameron & Huebsch, PLLC

(57) ABSTRACT

Methods and non-transitory machine-readable media associated with treatment plan identification are described. Treatment plan identification can include receiving first signaling configured to monitor user health data and receiving second signaling configured to monitor user behavior data. Treatment plan identification can include writing data that is based at least in part on a combination of the first signaling and the second signaling and identifying output data representative of a treatment plan for the user based at least in part on input data representative of the written data and additional user data. Output data representative of the treatment plan can be transmitted to a computing device accessible by the user, a computing device accessible by a provider, or both.

20 Claims, 5 Drawing Sheets

(56) References Cited

U.S. PATENT DOCUMENTS

| | | | | |
|---|---|---|---|---|
| 2021/0134461 | A1 | 5/2021 | Neumann | |
| 2021/0183520 | A1* | 6/2021 | Bates | G16H 20/60 |
| 2021/0233424 | A1 | 7/2021 | Lemme | |
| 2021/0241454 | A1 | 8/2021 | Min | |
| 2021/0241455 | A1* | 8/2021 | Min | A61B 6/504 |
| 2021/0241918 | A1 | 8/2021 | Kutzko | |
| 2021/0335498 | A1 | 10/2021 | Kulkarni et al. | |
| 2021/0407672 | A1* | 12/2021 | Zumbrun | G16H 10/20 |
| 2022/0051409 | A1 | 2/2022 | Maclellan et al. | |
| 2022/0406441 | A1 | 12/2022 | Linares et al. | |

* cited by examiner

TREATMENT PLAN IDENTIFICATION

PRIORITY INFORMATION

This application is a Continuation of U.S. application Ser. No. 17/411,801, filed Aug. 25, 2021, the contents of which are incorporated herein by reference.

TECHNICAL FIELD

The present disclosure relates generally to apparatuses, non-transitory machine-readable media, and methods associated with treatment plan identification.

BACKGROUND

Memory resources are typically provided as internal, semiconductor, integrated circuits in computers or other electronic systems. There are many different types of memory, including volatile and non-volatile memory. Volatile memory can require power to maintain its data (e.g., host data, error data, etc.). Volatile memory can include random access memory (RAM), dynamic random-access memory (DRAM), static random-access memory (SRAM), synchronous dynamic random-access memory (SDRAM), and thyristor random access memory (TRAM), among other types. Non-volatile memory can provide persistent data by retaining stored data when not powered. Non-volatile memory can include NAND flash memory, NOR flash memory, and resistance variable memory, such as phase change random access memory (PCRAM) and resistive random-access memory (RRAM), ferroelectric random-access memory (FeRAM), and magnetoresistive random access memory (MRAM), such as spin torque transfer random access memory (STT RAM), among other types.

Electronic systems often include a number of processing resources (e.g., one or more processing resources), which may retrieve instructions from a suitable location and execute the instructions and/or store results of the executed instructions to a suitable location (e.g., the memory resources). A processing resource can include a number of functional units such as arithmetic logic unit (ALU) circuitry, floating point unit (FPU) circuitry, and a combinatorial logic block, for example, which can be used to execute instructions by performing logical operations such as AND, OR, NOT, NAND, NOR, and XOR, and invert (e.g., NOT) logical operations on data (e.g., one or more operands). For example, functional unit circuitry may be used to perform arithmetic operations such as addition, subtraction, multiplication, and division on operands via a number of operations.

Artificial intelligence (AI) can be used in conjunction memory resources. AI can include a controller, computing device, or other system to perform a task that normally requires human intelligence. AI can include the use of one or more machine learning models. As described herein, the term "machine learning" refers to a process by which a computing device is able to improve its own performance through iterations by continuously incorporating new data into an existing statistical model. Machine learning can facilitate automatic learning for computing devices without human intervention or assistance and adjust actions accordingly.

DETAILED DESCRIPTION

Figure 1:
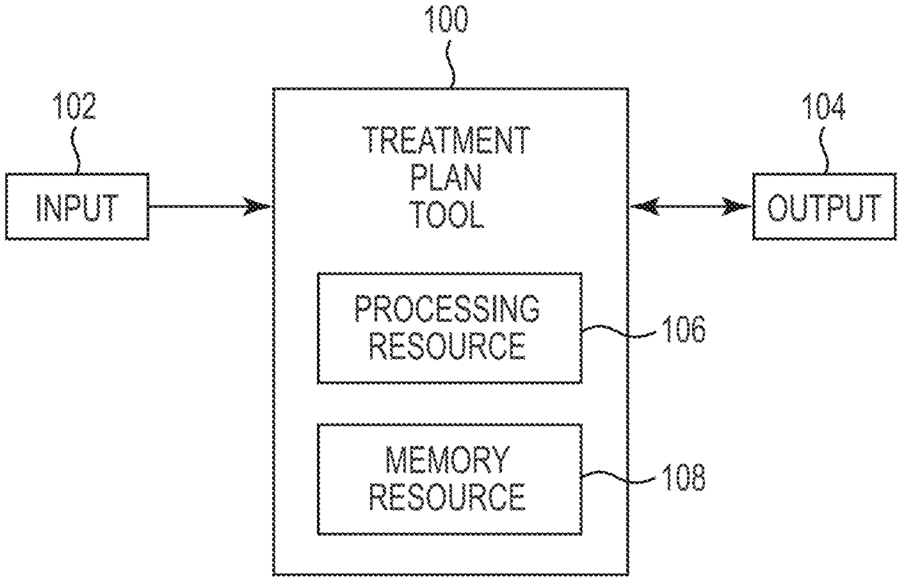
FIG. 1 is a functional diagram representing a treatment plan tool including a processing resource in communication with a memory resource for treatment plan identification in accordance with a number of embodiments of the present disclosure.

Apparatuses, machine-readable media, and methods related to treatment plan identification are described. Determining a cause and/or diagnosis of a physical, mental, or emotional disorder, disease, unwell feeling, or another malady can be challenging. A provider, such as a medical expert, healthcare provider, etc. may have biases toward an individual or a disorder or may not have access to all inputs affecting the individual, which can result in a misdiagnosis, inadequate treatment, etc. The individual may not know or realize what is causing his or her unwell feelings and may choose to incorrectly treat symptoms or ignore them.

Examples of the present disclosure can identify a treatment plan for a user by utilizing available health data and behaviors from the user, additional data from a user, data from a provider, a cloud service, databases including generic health information, or a combination thereof. As used herein, a treatment plan can include a diagnosis, a symptom-control plan, a symptom-treatment plan, a recommendation, a stimulation, goal feedback, or any combination thereof for a user. For instance, a treatment plan may include a determination that based on information associated with a user that the user likely is struggling with depression and can suggest immediate and future treatment. In another example, a treatment plan may indicate a user is likely suffering from a skin disorder and can contact a provider and suggest a treatment plan for symptom control. A user, for instance, can access an application on a mobile device and provide information about an ailment, and using information from a plurality of sources (e.g., medical devices, environmental sensors, behavioral sensors, etc.), a machine learning model can be utilized to determine a treatment plan for the user without bias.

Examples of the present disclosure can include a method for treatment plan identification including receiving, at a first processing resource, first signaling from a second processing resource configured to monitor user health data and receiving, at the first processing resource, second signaling from a third processing resource configured to monitor user behavior data. The method can include writing from the first processing resource to a memory resource coupled to the first processing resource data that is based at least in part on a combination of the first signaling and the second signaling.

In some examples, the method can include identifying at the first processing resource or at a different (e.g., a third) processing resource, output data representative of a treatment plan for the user based at least in part on input data representative of the written data and additional user data stored in a portion of the memory resource or other storage accessible by the first processing resource and transmitting the output data representative of the treatment plan to a fourth processing resource of a computing device accessible by the user, a fifth processing resource of a computing device accessible by a provider, or both.

In the following detailed description of the present disclosure, reference is made to the accompanying drawings that form a part hereof, and in which is shown by way of illustration how one or more embodiments of the disclosure can be practiced. These embodiments are described in sufficient detail to enable those of ordinary skill in the art to practice the embodiments of this disclosure, and it is to be understood that other embodiments can be utilized and that process, electrical, and structural changes can be made without departing from the scope of the present disclosure.

It is also to be understood that the terminology used herein is for the purpose of describing particular embodiments only and is not intended to be limiting. As used herein, the singular forms "a," "an," and "the" can include both singular and plural referents, unless the context clearly dictates otherwise. In addition, "a number of," "at least one," and "one or more" (e.g., a number of memory devices) can refer to one or more memory devices, whereas a "plurality of" is intended to refer to more than one of such things. Furthermore, the words "can" and "may" are used throughout this application in a permissive sense (i.e., having the potential to, being able to), not in a mandatory sense (i.e., must). The term "include," and derivations thereof, means "including, but not limited to." The terms "coupled," and "coupling" mean to be directly or indirectly connected physically or for access to and movement (transmission) of commands and/or data, as appropriate to the context.

The figures herein follow a numbering convention in which the first digit or digits correspond to the figure number and the remaining digits identify an element or component in the figure. Similar elements or components between different figures can be identified by the use of similar digits. For example, 102 can reference element "02" in FIG. 1, and a similar element can be referenced as 202 in FIG. 2. Analogous elements within a Figure may be referenced with a hyphen and extra numeral or letter. See, for example, elements 210-1 and 210-2 in FIG. 2. Such analogous elements may be generally referenced without the hyphen and extra numeral or letter. For example, elements 210-1 and 210-2 may be collectively referenced as 210. As will be appreciated, elements shown in the various embodiments herein can be added, exchanged, and/or eliminated so as to provide a number of additional embodiments of the present disclosure. In addition, the proportion and/or the relative scale of the elements provided in the figures are intended to illustrate certain embodiments of the present disclosure and should not be taken in a limiting sense.

FIG. 1 is a functional diagram representing a treatment plan tool 100 including a processing resource 106 in communication with a memory resource 108 for treatment plan identification in accordance with a number of embodiments of the present disclosure. The treatment plan tool 100 can be used to analyze and give feedback to a user about his or her physical health, mental health, or both. In some examples, the treatment plan tool 100 can be used to optimize an organization's workplace strategies with respect to assigning teams, projects, hiring, etc. Optimization of a workplace strategy can include connecting users (e.g., employees) with a best or most effective use of a situation or resource.

The treatment plan tool 100 can include, in some examples, the processing resource 106 in communication with the memory resource 108 that utilizes AI to determine a treatment plan. Put another way, the treatment plan tool 100 creates a plan of action for a user based on data available to the treatment plan tool 100 including, but not limited to, user health data (e.g., treatment history, allergies, current ailments, medication lists, symptoms, real-time health sensor data, etc.), user behavior data, additional user data, provider data, and a database of generic health data. Data shared with a treatment plan tool 100 may be encrypted, in some examples.

The treatment plan tool 100 may receive user data from the user, an authorized user (e.g., a guardian, caregiver, etc.), a healthcare provider, or any combination thereof via an application downloaded on a mobile device, such as a health application acting as an interface for users' data. For instance, a user's wearable device and/or monitors (e.g., smart watch, heart monitor, etc.) may provide data to the application or the user may manually input data into the application (e.g., address, phone number, emergency contacts, underlying conditions, current symptoms, current location, etc.). In some examples, a GPS or other location device on the mobile device may send location data to the application and/or treatment plan tool 100. The user data can be received at the treatment plan tool 100 and used in determining a treatment plan.

The treatment plan tool 100 (and associated AI (e.g., including machine learning model(s)) can be trained using a training dataset. For instance, the training dataset can include a set of examples used to fit parameters of the AI. For instance, the training dataset can include data associated with user health data, user behavior data, additional user data, provider data, and a database of generic health data. In some examples, the treatment plan tool 100 can also be trained using new input data (e.g., new data from users, providers, research data, etc., among others).

In some instances, the treatment plan tool 100 can utilize deep learning, computational imaging, a neural network, or any combination thereof. For example, deep learning can learn unsupervised from data that is unstructured or unlabeled. For instance, input data may include data from a plurality of source and may not be organized. In such an example, deep learning can be used to unravel large amounts of input data and process the input data to detect objects, recognize speech, translate language, make decisions, etc. Using deep learning, the treatment plan tool can learn without human supervision, drawing from input data that is both unstructured and unlabeled.

Deep learning can utilize a hierarchical level of neural networks (e.g., artificial neural networks) to carry out the process of machine learning. The neural networks can include nodes that enable the treatment plan tool 100 to process input data with a nonlinear approach. Deep learning, in some examples, can be used for computation imaging, which can include using an imperfect physical measurement and prior knowledge to deliver an estimate. For instance, unorganized input data can be received at the treatment plan tool 100, and computational imaging, deep learning, and neural networks can be used to process the input data and create a treatment plan for the user.

The treatment plan tool 100 can receive input data 102. As noted, the treatment plan tool 100 can receive input data 102 from a plurality of sources. Sources can include a database generic health information, user health data sources (e.g., personal tracking devices, personal medical devices, wearable devices, user health data, etc.), user behavior sources (e.g., keyboard sensors, image/voice recognition, cameras, etc.), providers (e.g., medical experts, research, etc.), and environmental sensors (e.g., weather sensors, cameras, temperature sensors, etc.), among others. For instance, the database of generic health information may include common symptoms, visuals, treatments, and other data associated with common ailments such as conjunctivitis, ear infections, etc. Environmental sensors, for instance, can include weather sensors or cameras that may indicate environmental conditions such as humidity, temperature, or potential allergens, among others.

User health data, additional user data, and user behavior data can be received from personal tracking devices such as a global positioning service (GPS) on a mobile device including a user location, a current travel speed, etc. User health data can be received from personal medical devices, sensor devices, or both (e.g., heartrate monitor, insulin pump, blood pressure monitor, etc.), and user behavior data can be received from sensor devices, tracking devices, or both (e.g., keyboard pressure sensor, cameras, chair sensors, bed sensors, diet sensors, etc.). In some examples, a user can manually input user data (e.g., additional user data, user heath data, user behavior data, etc.) such as address or birthday information and/or user health data and user behavior data such as current symptoms, current ailments, family health history, allergies, user health history, user behavioral history, current behavior, etc. via an application on a computing device and associated with the treatment plan tool 100.

In some examples, the input data 102 can be additional user data provided by a provider such as a medical expert or physician. For instance, the user's physician may receive as output data 104 a diagnosis for the user. The physician may then input additional user data (e.g., recommendations, prescriptions, etc.) as input data 102 into the treatment plan tool 100. The physician may have access to the treatment plan tool 100 via an application on a computing device, for instance. In some examples, a provider may provide input data 102 without receiving a diagnosis from the treatment plan tool 100.

Using the input data 102 received from the plurality of sources, the treatment plan tool 100 can determine a treatment plan for the user. Put another way, the treatment plan tool 100 can identify data representative of a treatment plan for the user using a machine learning model that considers the input data 102 representative of user health data, user behavior data, additional user health data, or any combination thereof.

In some examples, the treatment plan tool 100 may output data 104 that includes a diagnosis, a symptom-control plan, a symptom-treatment, an emotional quotient (EQ) of the user, or any combination thereof. For instance, the input data 102 when received and processed by the treatment plan tool 100 may indicate a user is suffering from high blood pressure in response to particular triggers such as email traffic (e.g., gathered using medical device, software tracking, keyboard pressure sensors, etc.) and, the treatment plan tool 100 may transmit output data 104 representative of a diagnosis to the user, a provider, or both (e.g., via an application). The provider may provide additional input data 102 to the treatment plan tool 100 responsive to receiving the diagnosis. The treatment plan tool 100, in some examples, may transmit output data 104 representative of a symptom-control plan (e.g., breath deeply, turn off computing device, etc.) or a symptom-treatment plan (e.g., take medication).

In some examples, the treatment plan tool 100 and associated AI and memory resource or storage can be updated based on the data associated with the input as discussed herein. For instance, new user health data (e.g., new symptoms), new user behavior data, new environmental data (e.g., changes in temperature, lighting, humidity, etc.), new additional user data (e.g., provider input, manual input), etc. can be saved in the memory resource 108 or storage and the treatment plan tool 100 can self-learn to update and improve accuracy and efficiency of treatment plan decisions.

In a non-limiting example, a user may have a disease triggered by stress (e.g., eczema, psoriasis, panic attack, etc.). The disease may be treated with suppressive medications that include possible side effects. Examples of the present disclosure can allow for monitoring of such a disease, along with the medications, to determine a treatment for the user. The user's health data and behavior data can be monitored (e.g., sleep monitors, keystroke monitors, sensors, wristbands, anklets, stress tests, etc.) and using a machine learning model, a personalized and unbiased treatment plan can be determined for the user. In some examples, stimulations can be presented to the user to determine triggers for particular behaviors, side effects, etc., and data collected from those stimulations can be used to determine an emotional quotient of the user, as well as combined with other data to determine a treatment plan for the user.

Figure 2:
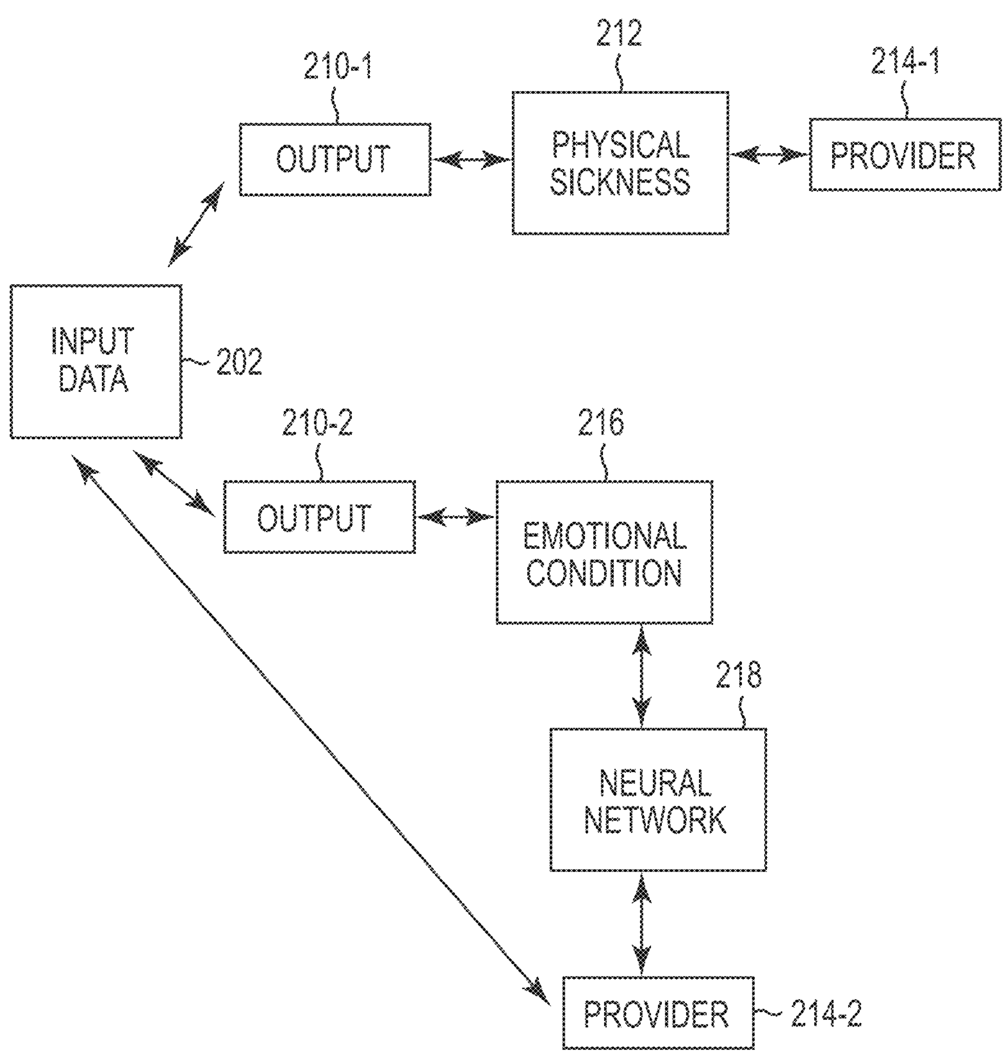
FIG. 2 is a flow diagram representing an example method for treatment plan identification in accordance with a number of embodiments of the present disclosure.

FIG. 2 is a flow diagram representing an example method for treatment plan identification in accordance with a number of embodiments of the present disclosure. The example method can be performed by a system such as the systems described with respect to FIGS. 3 and 4 or a treatment plan tool such as treatment plan tool 100 described with respect to FIG. 1.

At 202, input data can be received by a treatment plan tool. The input data can include user health data, user behavior data, additional user data, or any combination thereof, among others. The treatment plan tool can determine, based on the input data 202 what type of machine learning model to use to analyze the input data 202. For instance, at 210-1, the treatment plan tool can determine a physical sickness diagnosis and output that data to a provider at 214-1. For example, the treatment plan tool can determine the user has high blood pressure (e.g., based on wearable health monitor input data) and can output that to the provider 214-1, the user, or both. A suggested treatment (e.g., prescription, deep breathing, etc.) may be output to the provider 214-1, the user, or both, in some instances.

In another example, at 210-2, the treatment plan tool can determine an emotional condition diagnosis 216 and utilize a neural network 218 to analyze the input data 202. A result can be outputted to a provider at 214-2, and the provider can provide additional user input back to the treatment plan tool at 202. For instance, the treatment plan tool can determine the user is experiencing a nervous breakdown (e.g., based on wearable health monitor input data, sleep input data, eating habit input data, etc.), and pass that data to the provider 214-2 for further analysis, treatment plans, etc. In some examples, the treatment plan tool can utilize a neural network 218 to carry out the process of machine learning. The neural network 218 can enable the treatment plan tool to process input data 202 with a nonlinear approach. Deep learning and computational imaging may be utilized, in some examples, to further analyze the input data.

Figure 3:
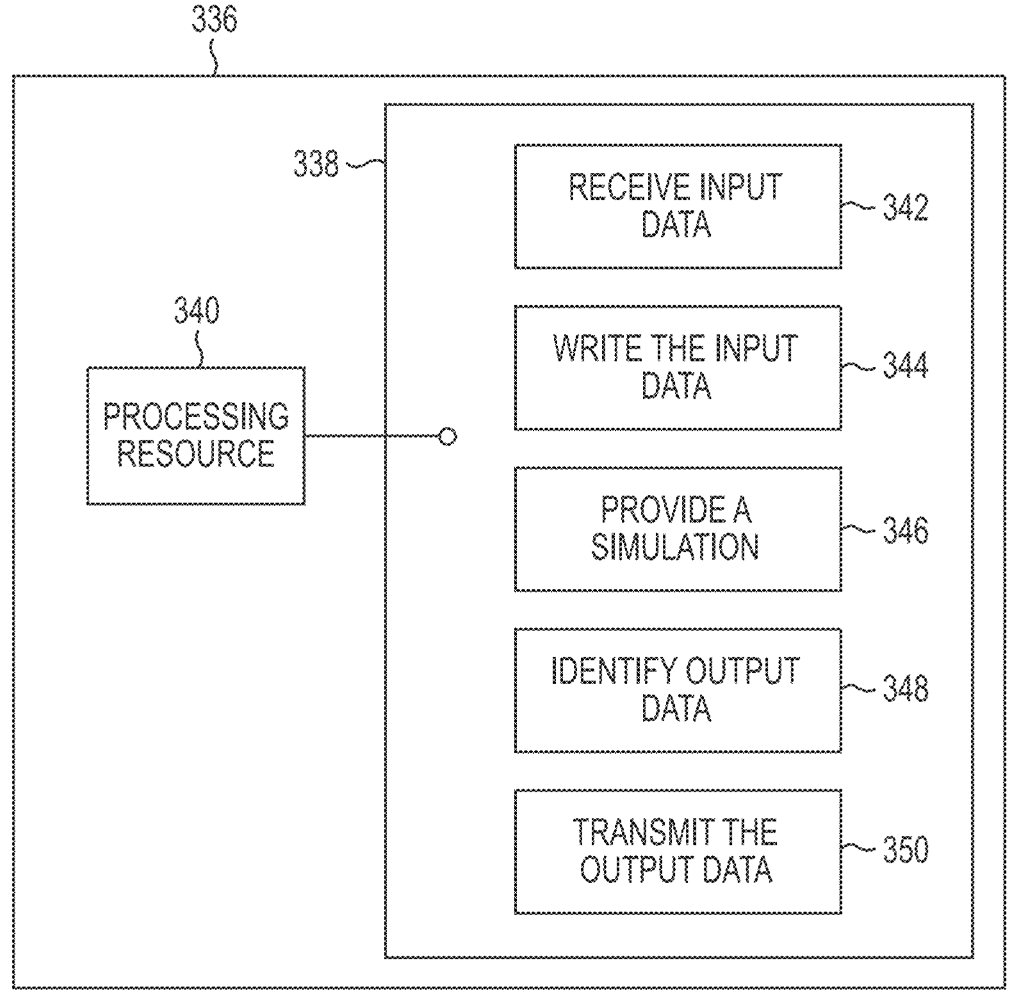
FIG. 3 is a functional diagram representing a processing resource in communication with a memory resource having instructions written thereon in accordance with a number of embodiments of the present disclosure.

FIG. 3 is a functional diagram representing a processing resource 340 in communication with a memory resource 338 having instructions 342, 344, 346, 348, 350 written thereon in accordance with a number of embodiments of the present disclosure. In some examples, the processing resource 340 and memory resource 338 comprise a system 336 such as a treatment plan tool (e.g., treatment plan tool 100 as illustrated in FIG. 1).

The system 336 illustrated in FIG. 3 can be a server or a computing device (among others) and can include the processing resource 340. The system 336 can further include the memory resource 338 (e.g., a non-transitory MRM), on which may be stored instructions, such as instructions 342, 344, 346, 348, 350. Although the following descriptions refer to a processing resource and a memory resource, the descriptions may also apply to a system with multiple processing resources and multiple memory resources. In such examples, the instructions may be distributed (e.g., stored) across multiple memory resources and the instructions may be distributed (e.g., executed by) across multiple processing resources.

The memory resource 338 may be electronic, magnetic, optical, or other physical storage device that stores executable instructions. Thus, the memory resource 338 may be, for example, non-volatile or volatile memory. For example, non-volatile memory can provide persistent data by retaining written data when not powered, and non-volatile memory types can include NAND flash memory, NOR flash memory, read only memory (ROM), Electrically Erasable Programmable ROM (EEPROM), Erasable Programmable ROM (EPROM), and Storage Class Memory (SCM) that can include resistance variable memory, such as phase change random access memory (PCRAM), three-dimensional cross-point memory, resistive random access memory (RRAM), ferroelectric random access memory (FeRAM), magnetoresistive random access memory (MRAM), and programmable conductive memory, among other types of memory. Volatile memory can require power to maintain its data and can include random-access memory (RAM), dynamic random-access memory (DRAM), and static random-access memory (SRAM), among others.

In some examples, the memory resource 338 is a non-transitory MRM comprising Random Access Memory (RAM), an Electrically-Erasable Programmable ROM (EEPROM), a storage drive, an optical disc, and the like. The memory resource 338 may be disposed within a controller and/or computing device. In this example, the executable instructions 342, 344, 346, 348, 350 can be "installed" on the device. Additionally, and/or alternatively, the memory resource 338 can be a portable, external or remote storage medium, for example, that allows the system to download the instructions 342, 344, 346, 348, 350 from the portable/external/remote storage medium. In this situation, the executable instructions may be part of an "installation package". As described herein, the memory resource 338 can be encoded with executable instructions for determining a treatment plan. In some examples, the system 336 and/or memory resource 338 can include a storage engine such as a heterogeneous-memory storage engine (HSE) or other engine configured to facilitate access to different (e.g., multiple) memory/media types and can handle larger workloads and/or neural netorks. User data and trained models, in some examples, can be stored in the memory resource 338 for near-real-time recommendations.

The instructions 342, when executed by a processing resource such as the processing resource 340 (herein after referred to as the "first processing resource 340"), can include instructions to receive at the first processing resource 340, the memory resource 338, or both, a plurality of input data from a plurality of sources, the plurality of sources comprising at least two of a mobile device of a user, a medical device, a portion of the memory resource or other storage, manually received input, and device sensors. The plurality of input data, for instance, can include user health data, user behavior data, or both. User health data can include data associated with mental health of the user, physical health of the user, or both. For instance, user health data may include previous diagnoses, current monitored actions (e.g., heartrate, lung capacity, etc.), among others. User behavior data can include data associated with actions and reactions of the user such as heartrate increases in response to particular stimuli, exercise habits, etc.

In some examples, the memory resource 338 or other storage accessible by the first processing resource 340 can include additional user data. The additional user data can include, for instance, previously successful treatment plans associated with the user. For example, a user may have had previous success treating depression with a particular medication and exercise. In some instances, the additional user data can be provided by the user or another device. For instance, data (e.g., user health data, user behavior data, additional user data, etc.) may be manually entered via an application of a mobile device for sending to the first processing resource 340 or automatically (e.g., with little or no human intervention) to the first processing resource 340.

The instructions 344, when executed by a processing resource such as the first processing resource 340, can include instructions to write from the first processing resource 340 to the memory resource 338 the received input data. Such data can be stored in the memory resource 338 for use in determining a treatment plan for the user.

The instructions 346, when executed by a processing resource such as the processing resource 340, can include instructions to provide a stimulation to a second processing resource of a computing device accessible by the user based at least in part on input data representative of the written data. For instance, the stimulation may include a movie, email, role play, etc. to observer trigger material for the user. For instance, a user can be provided with a baseline to modify (e.g., based on cultural background, genetic background, how the user was raised, etc.) and the trigger material can be used to determine how a user reacts in particular situations. In some examples, results of the stimulations can include an emotional quotient score for the user determined using a machine learning model.

The instructions 348, when executed by a processing resource such as the processing resource 340, can include instructions to identify, using a trained machine learning model and at the first processing resource 340 or a third processing resource, output data representative of a treatment plan including a diagnosis for the user, a symptom-control plan, a symptom-treatment plan, or any combination thereof based at least in part on input data representative of the written data and results of the stimulation received at the first processing resource. For instance, a user suffering a panic attack in response to an email from a particular coworker may have responded in a similar manner during a stimulation but was calmed with deep breathing and music. In such an example, deep breathing and music may be included in the treatment plan, among other treatment strategies. In such an example, the treatment plan may include programming the user's computing device such that soothing music is played when an email from the particular coworker is opened.

In some instance, the instructions are executable to identify the output data representative of the treatment plan based at least in part on generic health information stored in a portion of the memory resource 338 or other storage accessible by the first processing resource 340. For instance, a database of generic health information may be maintained and updated including common ailments, associated treatments, and associated symptoms.

In some instances, the identification includes the use of a trained machine learning model. For example, the trained machine learning model can use all or some of the input data to determine one or more treatment plans for the user. In some examples, computational imaging, a neural network, or both can be used during identification of the treatment plan. For instance, because a large amount of input data is received, and the input data includes sensitive data, computational imaging and/or a neural network may be used to simplify the input data and make suggestions and then provide suggestions for treatment.

The instructions 350, when executed by a processing resource such as the processing resource 340, can include instructions to transmit the output data representative of the treatment plan to the second processing resource, a fourth processing resource of a computing device accessibly by a provider, or both. For example, upon identification of the treatment plan, the user may be alerted via an application. The alert may include instructions, in some examples, to execute the treatment plan (e.g., breathe deeply, chew an aspirin, wait for Emergency Vehicle A to arrive, health care provider B has been alerted, etc.).

Figure 4:
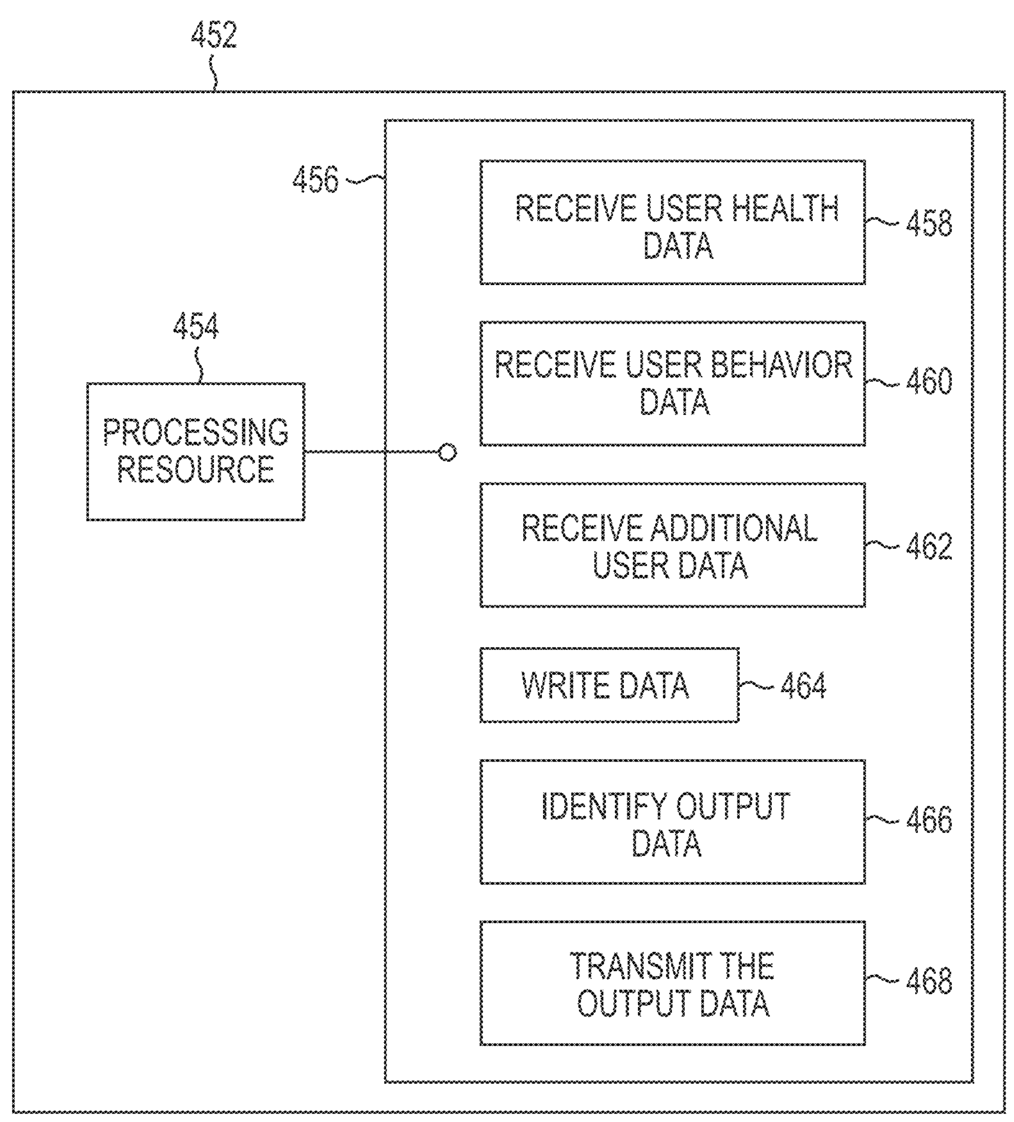
FIG. 4 is another functional diagram representing a processing resource in communication with a memory resource having instructions written thereon in accordance with a number of embodiments of the present disclosure.

FIG. 4 is another functional diagram representing a processing resource 454 in communication with a memory resource 456 having instructions 458, 460, 462, 464, 466, 468 written thereon in accordance with a number of embodiments of the present disclosure. In some examples, the processing resource 454 (herein after referred to as "the first processing resource 454") and the memory resource 456 may be analogous to processing resource 340 and memory resource 338, respectively, as described with respect to FIG. 3. In some examples, the processing resource 454 and the memory resource 456 comprise a system 452 such system 336 illustrated in FIG. 3, treatment plan tool 100, illustrated in FIG. 1, or both. In some example, the memory resource 456 comprises a plurality of memory resource to which access is facilitated via a storage engine such as an HSE.

The instructions 458, when executed by a processing resource such as the processing resource 454, can include instructions to receive at the first processing resource 454, the memory resource 456, or both, user health data via first signaling configured to monitor user health data, via signaling associated with a second processing resource of a mobile device of the user, or both. For instance, the user health data can be received from a heart monitor, insulin pump, smart watch, or other health monitoring device. The user health data may be entered manually by a user, for instance via an application on a mobile device. In some examples, the user health data can include health symptoms, a health event (e.g., heart attack, high blood pressure, slow breathing, etc.), personal health information of the user (e.g., preexisting conditions, allergies, etc.), identifying information of the user (e.g., name, address, birthdate, etc.), a location of the user, data collected by a health monitor (e.g., heart rate, etc.), manually input data of the user, or any combination thereof.

The instructions 460, when executed by a processing resource such as the first processing resource 454, can include instructions to receive at the first processing resource 454, the memory resource 456, or both, user behavior data via second signaling configured to monitor user behavior data, via signaling associated with the second processing resource of the mobile device of the user, or both. User behavior data, for instance, can be received from sensor devices, tracking devices, or both (e.g., keyboard pressure sensor, cameras, chair sensors, bed sensors, diet sensors, etc.). In some examples, a user can manually input user behavior data such as user behavioral history, current behavior, etc. via an application.

The instructions 462, when executed by a processing resource such as the first processing resource 454, can include instructions to receive at the first processing resource 454, the memory resource 456, or both, additional user data via third signaling associated with a third processing resource of a computing device accessible by a provider. In some examples, the additional user data can be stored in a portion of the memory resource 456 or other storage accessible by the first processing resource 454. The additional user data, for instance can include current prescription medications, user location, user traveling speed, previously successful and/or unsuccessful treatment plans, etc.

The instructions 464, when executed by a processing resource such as the first processing resource 454, can include instructions to write from the first processing resource 454 to the memory resource 456 the user health data, user behavior data, and the additional user data. In some examples, the memory resource 456 or storage can be updated using the written data. The updated memory resource 456 or storage, along with updates to AI can allow for self-learning and improved accuracy, efficiency, and consistency in treatment plan determinations.

The instructions 466, when executed by a processing resource such as the first processing resource 454, can include instructions to identify at the first processing resource 454 or a second processing resource, output data representative of a treatment plan for the user using a trained machine learning model, a neural network, input data representative of the written user health data, the written user behavior data, and the written additional user data. In some examples, the trained machine learning model can include a deep learning machine learning model using computational imaging. In some instances, a database of generic health data can be utilized. The database, for instance, can be part of the memory resource 456 or other storage communicatively coupled to the medium and can include generic health symptoms and associated diagnoses and treatments.

In some examples, identifying the output data can include determining a diagnosis for the user, determining a prescription for the user, and/or determining a treatment location for the user, among other determinations, based on the user health data, the user behavior data, the additional user data, the database of generic health data, or any combination thereof. In some examples, identifying the output data can include scheduling an appointment with a health care provider. For instance, if a determination is made that the user may not need immediate treatment, an appointment can be suggested or automatically made.

The instructions 468, when executed by a processing resource such as the first processing resource 454, can include instructions to transmit (e.g., via a radio) the output data representative of the treatment plan to the user, the provider, an authorized user, or any combination thereof. The output data can include, for instance, a diagnosis, a symptom-control plan, a symptom-treatment plan, or any combination thereof. For instance, if it is determined the user should be treated immediately, the treatment plan can be transmitted to the user (e.g., via the application on the user's mobile device), as well as to a health care provider and/or authorized user (e.g., guardian, power of attorney, etc.).

In some examples, the output data representative of the treatment plan can be updated as new input data representative of the written user health data, the written user behavior data, and the written additional user data is received. For instance, as new data is received at a treatment plan tool, a treatment plan can be updated accordingly. The updated output data can be transmitted to the user, the provider, the authorized user, or any combination thereof.

In some examples, the treatment plan can be associated with an organization (e.g., a workplace). For instance, the user can be an employee of the organization, and the output data can include a strategy plan for the organization. Employees in an organization may undergo stimulations, and the results can be used to analyze team dynamics, form teams for certain projects (e.g., emotional quotient A may work well with emotional quotient B), hiring, etc.

Figure 5:
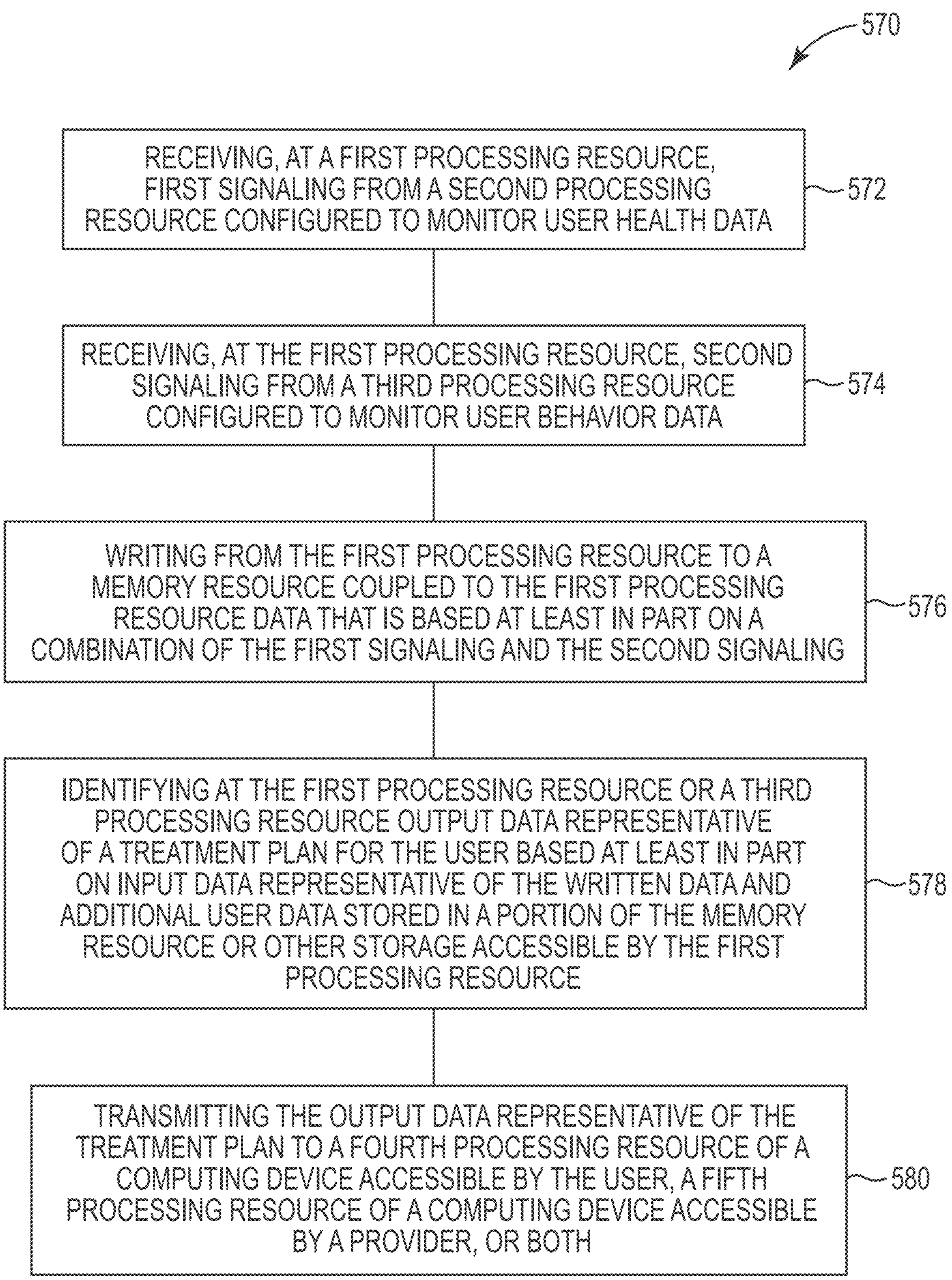
FIG. 5 is another flow diagram representing an example method for treatment plan identification in accordance with a number of embodiments of the present disclosure.

FIG. 5 is another flow diagram representing an example method 570 for treatment plan identification in accordance with a number of embodiments of the present disclosure. The method 570 can be performed by a system such as the systems described with respect to FIGS. 3 and 4 or a treatment plan tool such as treatment plan 100 described with respect to FIG. 1.

At 572, the method 570 can include receiving, at a first processing resource, first signaling from a second processing resource configured to monitor user health data. For instance, blood pressure, heart rate, eye activity, skin health/color, motion analysis, etc. may be received from medical devices and/or health monitors, sensors, or both. In some examples, electroencephalography, measuring the aforementioned and other body parameters, electric impulses in the user's nervous system, or any combination thereof, as well as any changes, may provide data received at the first processing resource.

At 574, the method 570 can include receiving, at the first processing resource, second signaling from a third processing resource configured to monitor user behavior data. User behavior data, for instance, may be determined using image recognition, voice recognition, or a combination thereof to determine changes in a user's lips, forehead, limping, body posture of the user's shoulders or chest, typing strokes, etc. which can indicate a user's mental and/or emotional state.

The method 570, at 576, can include writing from the first processing resource to a memory resource coupled to the first processing resource data that is based at least in part on a combination of the first signaling and the second signaling. The written data can be saved at the memory resource for use in determination of a current or future treatment plan.

In some examples, the method 570 can include receiving at the first processing resource via an application of the computing device accessible by the user, manual input from the user comprising user health data, user behavior data, additional user data, or a combination thereof and writing from the first processing resource to the memory resource coupled to the first processing resource data that is based at least in part on a combination of the first signaling, the second signaling, and the manual input. For instance, a user may be able to enter data the first processing resource had not previously received, for instance, past diagnoses, current or past moods, current or past prescriptions, etc.

The method 570, at 578 can include identifying at the first processing resource or at a different (e.g., at a third) processing resource, output data representative of a treatment plan for the user based at least in part on input data representative of the written data and additional user data stored in a portion of the memory resource or other storage accessible by the first processing resource. In some instances, identifying the output data can include utilizing a trained machine learning model to identify the output data representative of the treatment plan based on data associated with the first and the second signaling, generic health data, and previously received signaling and associated data associated with treatment plans. For instance, data previous stored in the memory resource may be considered in determining a treatment plan.

In some examples, identifying the output data representative of the treatment plan comprises utilizing a trained machine learning model, computational imaging, and a neural network to identify the output data representative of the treatment plan. For instance, in some examples, a stimulation can be provided to the fourth processing resource of the computing device accessible by the user, and the output data representative of the treatment plan can be based at least in part on received results of the stimulation.

For instance, the method 570 can include the consideration of a user's goal (e.g., target job, treating stress triggers, etc.). For instance, the method 570 can include receiving at the first processing resource via an application of the computing device accessible by the user, a goal of the user. An iterative process can then be performed and can continue, for instance, until an indication is received at the first processing resource that the goal is reached.

For instance, the iterative process can include providing a stimulation based on the goal to the fourth processing resource of the computing device accessible by the user, identifying at the first processing resource or the different processing resource, output data representative of the treatment plan for the user based at least in part on input data representative of the written data, the additional user data stored in a portion of the memory resource or other storage accessible by the first processing resource, and received results of the stimulation, and transmitting the output data representative of the treatment plan including feedback for reaching the goal to the fourth processing resource of a computing device accessible by the user, a fifth processing resource of a computing device accessible by a provider, or both.

Put another way, a machine learning model may be triggered with stimulations such as case studies that the user undergoes. The user may watch a movie, play an augmented reality game, or answer emails from a particular individual, among other stimulations. Based on the user's goal and using stored data, the machine learning model can use data received during the stimulation to determine an emotional quotient score of the user and compare that score to scores of a general population or a population having particular demographics (e.g., similar to those of the user).

In some examples, the user may practice using the stimulations because the machine learning model can take the target goal and modify the stimulations accordingly. The machine learning model may suggest positive behavioral changes for the user to reach the goal. In some instances, continuous or near-continuous feedback may be provided to the user, for instance via an application.

At 580, the method 570 can include transmitting the output data representative of the treatment plan to a fourth processing resource of a computing device accessible by the user, a fifth processing resource of a computing device accessible by a provider, or both. For example, the output data can include output data representative of a diagnosis, a symptom-control plan, a symptom-treatment plan, an emotional quotient of the user, or any combination thereof. The output data may also include the feedback determined using the stimulations and machine learning model. The user, an authorized user, a healthcare provider, or any combination thereof may receive the output data, for instance.

Although specific embodiments have been illustrated and described herein, those of ordinary skill in the art will appreciate that an arrangement calculated to achieve the same results can be substituted for the specific embodiments shown. This disclosure is intended to cover adaptations or variations of one or more embodiments of the present disclosure. It is to be understood that the above description has been made in an illustrative fashion, and not a restrictive one. Combination of the above embodiments, and other embodiments not specifically described herein will be apparent to those of skill in the art upon reviewing the above description. The scope of the one or more embodiments of the present disclosure includes other applications in which the above structures and processes are used. Therefore, the scope of one or more embodiments of the present disclosure should be determined with reference to the appended claims, along with the full range of equivalents to which such claims are entitled.

In the foregoing Detailed Description, some features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A method, comprising:

receiving, at a first processing resource, first signaling from a second processing resource configured to monitor user health data;

receiving, at the first processing resource, second signaling from a third processing resource configured to monitor user behavior data;

writing from the first processing resource to a memory resource coupled to the first processing resource data that is based at least in part on a combination of the first signaling and the second signaling;

identifying, utilizing a trained machine learning model, deep learning, computational imaging, and neural networks at the first processing resource or at a third processing resource, output data representative of a treatment plan for the user based at least in part on input data representative of the written data and additional user data stored in a portion of the memory resource or other storage accessible by the first processing resource; and transmitting the output data representative of the treatment plan to a fourth processing resource of a computing device accessible by the user, a fifth processing resource of a computing device accessible by a provider, or both.

2. The method of claim 1, wherein identifying the output data representative of the treatment plan comprises utilizing the trained machine learning model to identify the output data representative of the treatment plan based on data associated with the first and the second signaling, generic health data, and previously received signaling and data associated with treatment plans.

3. The method of claim 1, wherein transmitting the output data representative of the treatment plan comprises transmitting output data representative of an emotional quotient of the user, wherein the emotional quotient is determined utilizing data collected from a plurality of stimulations provided to the user.

4. The method of claim 1, wherein transmitting the output data representative of the treatment plan comprises transmitting output data representative of a diagnosis, a symptom-control plan, a symptom-treatment plan, or any combination thereof.

5. The method of claim 1, further comprising:

providing a stimulation to the fourth processing resource of the computing device accessible by the user; and identifying at the first processing resource or at the third processing resource output data representative of the treatment plan for the user based at least in part on input data representative of the written data, the additional user data stored in a portion of the memory resource or other storage accessible by the first processing resource and received results of the stimulation.

6. The method of claim 1, further comprising:

receiving at the first processing resource via an application of the computing device accessible by the user, manual input from the user comprising user health data, user behavior data, additional user data, or a combination thereof; and writing from the first processing resource to the memory resource coupled to the first processing resource data that is based at least in part on a combination of the first signaling, the second signaling, and the manual input.

7. The method of claim 1, further comprising:

receiving at the first processing resource via an application of the computing device accessible by the user, a goal of the user; and iteratively, until indication is received at the first processing resource that the goal is reached:

providing a stimulation based on the goal to the fourth processing resource of the computing device accessible by the user;

identifying at the first processing resource output data representative of the treatment plan for the user based at least in part on input data representative of the written data, the additional user data stored in a portion of the memory resource or other storage accessible by the first processing resource, and received results of the stimulation; and transmitting the output data representative of the treatment plan including feedback for reaching the goal to the fourth processing resource of a computing device accessible by the user, a fifth processing resource of a computing device accessible by a provider, or both.

8. A non-transitory machine-readable medium comprising a first processing resource in communication with a memory resource having instructions executable to:

receive at the first processing resource, the memory resource, or both, a plurality of input data from a plurality of sources, the plurality of sources comprising at least two of a mobile device of a user, a medical device, a portion of the memory resource or other storage, manually received input, and device sensors;

write from the first processing resource to the memory resource the received input data;

provide a stimulation to a second processing resource of a computing device accessible by the user based at least in part on input data representative of the written data;

identify, using a trained machine learning model, deep learning, computational imaging, and a neural network at the first processing resource or a third processing resource, output data representative of a treatment plan including a diagnosis for the user, a symptom-control plan, a symptom-treatment plan, or any combination thereof based at least in part on input data representative of the written data and results of the stimulation received at the first processing resource; and transmit the output data representative of the treatment plan to the second processing resource, a fourth processing resource of a computing device accessible by a provider, or both.

9. The medium of claim 8, wherein the plurality of input data comprises user health data, user behavior data, or both.

10. The medium of claim 9, wherein:

the user health data comprises data associated with mental health of the user, physical health of the user, or both; and the user behavior data comprises data associated with actions and reactions of the user.

11. The medium of claim 8, further comprising the instructions executable to identify the output data representative of the treatment plan based at least in part on additional user data stored in a portion of the memory resource or other storage accessible by the first processing resource including previously successful treatment plans associated with the user.

12. The medium of claim 8, further comprising the instructions executable to identify the output data representative of the treatment plan based at least in part on generic health information stored in a portion of the memory resource or other storage accessible by the first processing resource.

13. The medium of claim 8, further comprising the instructions executable to transmit output data representative of an emotional quotient of the user, wherein the emotional quotient is determined utilizing data collected from a plurality of stimulations provided to the user.

14. A non-transitory machine-readable medium comprising a first processing resource in communication with a memory resource having instructions executable to:

receive at the first processing resource, the memory resource, or both, user health data via first signaling configured to monitor user health data, via signaling associated with a second processing resource of a mobile device of the user, or both;

receive at the first processing resource, the memory resource, or both, user behavior data via second signaling configured to monitor user behavior data, via signaling associated with the second processing resource of the mobile device of the user, or both;

receive at the first processing resource, the memory resource, or both, additional user data via third signaling associated with a third processing resource of a computing device accessible by a provider;

write from the first processing resource to the memory resource the user health data, the user behavior data, and the additional user data;

identify at the first processing resource or a second processing resource, output data representative of a treatment plan for the user using a trained machine learning model, a neural network, deep learning, computational imaging, input data representative of the written user health data, the written user behavior data, and the written additional user data; and transmit the output data representative of the treatment plan to the user, the provider, an authorized user, or any combination thereof.

15. The medium of claim 14, wherein the output data representative of the treatment plan comprises a diagnosis, a symptom-control plan, a symptom-treatment plan, or any combination thereof.

16. The medium of claim 14, wherein the memory resource comprises a plurality of memory resources to which access is facilitated via a storage engine.

17. The medium of claim 14, wherein the user is an employee of an organization and the output data representative of the treatment plan comprises a strategy plan for the organization.

18. The medium of claim 14, further comprising the instructions executable to:

update the output data representative of the treatment plan as new input data representative of the written user health data, the written user behavior data, and the written additional user data is received; and transmit the updated output data representative of the treatment plan to the user, the provider, the authorized user, or any combination thereof.

19. The medium of claim 14, further comprising instructions executable to identify at the first processing resource or the second processing resource, output data representative of a treatment plan for the user using a trained machine learning model, a neural network, input data representative of the written user health data, the written user behavior data, the written additional user data, and input representative of a database of generic health data, wherein the database of generic health data is part of the memory resource or other storage communicatively coupled to the medium and comprises generic health symptoms and associated diagnoses and treatments.

20. The medium of claim 14, further comprising the instructions executable to transmit output data representative of an emotional quotient of the user, wherein the emotional quotient is determined utilizing data collected from a plurality of stimulations provided to the user.

* * * * *